United States Patent [19]

Nakai et al.

[11] Patent Number: 5,051,240
[45] Date of Patent: Sep. 24, 1991

[54] VOLATILE COMPONENT DETECTOR WITH SOCKET FOR SAMPLE RECEPTACLE

[75] Inventors: Takayuki Nakai; Tadahisa Kono, both of Tokyo, Japan

[73] Assignee: Kirin Beer Kabushiki Kaisha, Tokyo, Japan

[21] Appl. No.: 531,862

[22] Filed: Jun. 1, 1990

[30] Foreign Application Priority Data

Jun. 22, 1989 [JP] Japan .................................. 1-73444
Sep. 27, 1989 [JP] Japan .................................. 1-113164

[51] Int. Cl.⁵ ...................... G01N 27/00; G01N 27/07
[52] U.S. Cl. ......................................... 422/83; 422/98; 422/102; 73/23.34; 73/864.91
[58] Field of Search ............................ 422/83, 98, 102; 340/632, 634; 73/23.34, 31.06, 31.05, 864.81, 864.82, 864.83, 864.84, 864.85, 864.91

[56] References Cited

U.S. PATENT DOCUMENTS

| | | | |
|---|---|---|---|
| 4,298,574 | 11/1981 | Bohl | 422/98 X |
| 4,770,025 | 9/1988 | Ehara | 422/83 X |
| 4,770,027 | 9/1988 | Ehara | 422/83 X |
| 4,801,546 | 1/1989 | Ackland | 422/102 X |
| 4,884,435 | 12/1989 | Ehara | 422/83 X |

Primary Examiner—Robert J. Warden
Assistant Examiner—Stephanie Blythe
Attorney, Agent, or Firm—Ladas & Parry

[57] ABSTRACT

A volatile component detector having a sensor platform fixed inside a main body of a volatile component detector comprises: a sample receptacle which is engagedly supported to a side of a bottom surface of the sensor platform, and the sensor platform has a receptacle support hole which enables a sample receptacle to engage with and be supported in a status of variable and close contact. An odor sensor is set on an inner bottom surface of the receptacle support hole and has its detector portion protruding through the receptacle support hole. The sample receptacle has an opening which enables the insertion of a detector portion of the odor sensor into a top plate. Thus, detector portion of the odor sensor can be inserted into the sample receptacle from the opening when the sample receptacle is engaged with and supported by the receptacle hole of the sensor platform.

2 Claims, 7 Drawing Sheets

VOLATILE COMPONENT DETECTOR WITH SOCKET FOR SAMPLE RECEPTACLE

BACKGROUND OF THE INVENTION

The present invention relates to a volatile component detector.

In the food industry, in the process for the manufacture of foodstuffs in which emphasis is placed on the odor and the freshness and other qualities of foodstuffs, judgments as to quality as determinable by the relationship with odor have been conventionally performed by the human sense of smell. However, by this method, it is difficult to obtain precise data because of individual differences in the sense of smell, and quantitative data could not be obtained.

Recently, there has been the development of gas sensors and odor sensors that use voltage changes or current resistance values to detect when odor components having volatile components attach to them, and these have been used in detection apparatus that enables an objective assessment of the concentration of odor by the analysis of these changes in the status. It is therefore possible to promptly obtain accurate odor data (see, for example, Japanese Patent Laid-Open Publication No. 222154/1987, Japanese Patent Laid-Open Publication No. 259250/1989, and Japanese Utility Model Laid-Open Publication No. 156871/1987).

However, in a detection apparatus using a conventional odor sensor, as shown in outline in FIG. 12 for example, the odor sensor S is disposed so as to face a surface inside a detection chamber 2 of a detector 1 that is formed of a material such as stainless steel, for example, for which the attachment of odor is difficult. A sample for which the odor is to be detected is placed in a sample receptacle 3 inside the detection chamber 2, the door 4 of the detection chamber 2 is closed and the volatile components dispersed from the sample fill inside the detection chamber 2 were they are detected by the odor sensor S to therefore allow the detection of the concentration of the volatile components or their identification. When the odor molecules given off by the sample came into contact with the sensor S, the electrical resistance changes downwardly immediately and the current flowing through the circuit changes. This current is then converted into a voltage, amplified, and its value is displayed by the digital indicator, and printed by the printer.

In such a conventional detector, the structure is such that the sample for which the odor is to be detected is placed in a sample receptacle which is placed into and taken out of the detection chamber. Therefore, this necessitates the provision of an opening portion having a size which is large enough for a hand to reach into the detection chamber. Because of this, the volume of the detection chamber becomes larger and it takes a long time for volatile components dispersed from the sample to fill inside the detection chamber. The result is that a long time is taken for detection. In addition, it is also necessary to replace the air inside the detection chamber with odorless air so that the following detection can be performed but residual odor from the previous detection remains inside the detection chamber if the detection chamber is large, and this causes the problem of the residual odor influencing the accuracy of the data of the following odor detection. Even if activated charcoal is used as a deodorizing agent, it requires approximately one day for the residual odor to be completely removed, and therefore the efficiency is poor. Not only this, since there are no standards for judging whether or not complete deodorization has been achieved, it is easy for errors to occur in the following detection. Moreover, it is not sufficient to use a material such as Teflon (registered trademark) to which it is difficult for odors to attach, as the material for the detection chamber, since if there is a portion to which odor from a previous measurement still remains, then it will be impossible for this not to influence the following measurement. In addition, the odor will enter the detection chamber even if repeated measurement is performed for the same odor and this will become a cause of scattering in the measurement results with respect to the actual concentration. Accordingly, in delicate measurements where the identification of odors has to be performed, there has been the problem of sufficient accuracy being unobtainable.

In the light of these problems, the present invention has as an object the provision of a volatile component detection apparatus that has the number of parts in the configuration between the odor sensor and a sample receptacle that can be easily returned to an odorless state, that has an extremely small amount of residual odor that influences following measurements, that takes a short time to be deodorized after a measurement, and that can promote the efficiency of the measurement task.

SUMMARY OF THE INVENTION

In order to eliminate the problems inherent in the conventional art as described above, it is an object of the present invention to provide a sensor platform fixed inside a main body of a volatile component detector, and a sample receptacle that is engagedly supported to a side of a bottom surface of a sensor platform. The sensor platform has a receptacle support hole that enables a sample receptacle to engage with and be supported in a status of variable and close contact. An odor sensor on an inner bottom surface of the receptacle support hole has its detector portion protruding through said receptacle support hole and the sample receptacle has an opening that enables the insertion of a detector portion of the odor sensor into a top plate. So that a detector portion of an odor sensor can be inserted into a sample receptacle from the opening when the sample receptacle is engaged with and supported by the receptacle hole of said sensor platform.

Moreover, according to other object of the present invention, an absorption material of activated charcoal fiber or the like is added to an inner surface of a covering box mounted in an airtight manner so as to cover an exposed portion and an engagement portion of the sample receptacle at a lower portion of the volatile component detector so that odors in the atmosphere surrounding the detector do not influence the results of detection. Thus, a zero point is provided for the odor sensor so that the reproducibility of the odor detection is heightened.

When actual measurements are performed, the sample that is to be detected is placed inside the sample receptacle and the sample receptacle is engaged with and supported by a receptacle support hole from the side of the bottom of the sensor platform and the detector portion of the odor sensor is inserted into the sample receptacle from an opening in the top plate of the sample receptacle. So that the volatile components dispersed from the sample inside the sample receptacle come into contact with the detector portion of the odor sensor and the measurement starts. When this occurs, the inner surface of the receptacle support hole in the sensor platform is covered by the outer surface of the sample receptacle and so the odor that is dispersed from the sample does not come into contact with the inner surface of the receptacle support hole to therefore prevent residual odor adhering after the measurement has been completed and the sample receptacle has been removed. It is therefore necessary for only the sample receptacle to be deodorized before the commencement of the following measurement. In addition, if the covering box is used, then even if the air inside the room enters the covering box when the sample receptacle is taken off and replaced when the samples are exchanged, any odors are absorbed and removed by the deodorizing material on the inner surface. So that there is less influence with respect to the odor sensor and so that fluctuations in the zero return point of the odor sensor do not occur. The measurement reproducibility is therefore raised.

A preferred embodiment of the present invention will become understood from the following detailed description referring to the accompanying drawings.

DETAILED DESCRIPTION OF THE INVENTION

Figure 1:
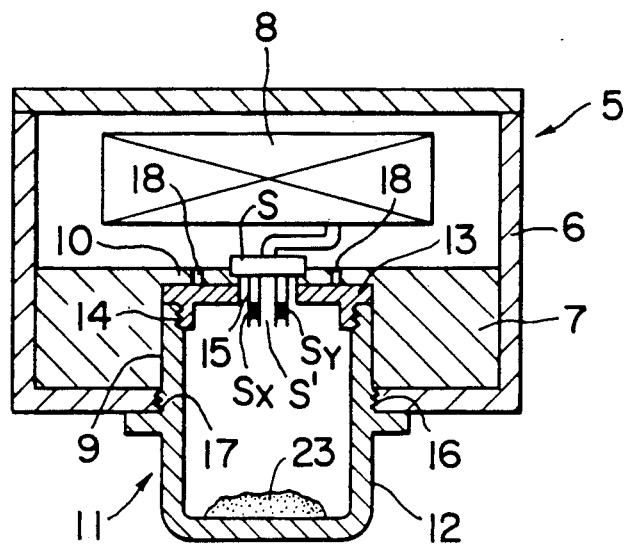
FIG. 1 is a longitudinal sectional view of one embodiment according to the present invention.
Figure 2:
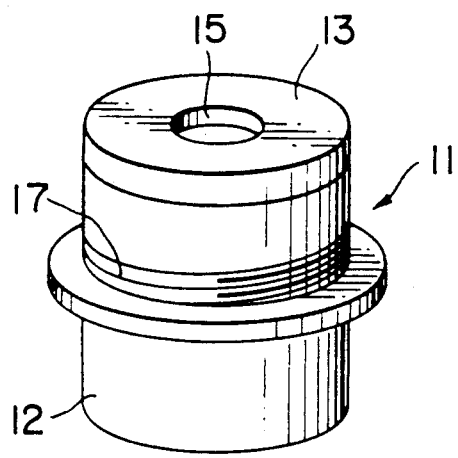
FIG. 2 is a perspective view of the sample receptacle shown in FIG. 1.

Referring to FIGS. 1 and 2 a detector unit 5 has a configuration comprising an external housing 6 having a box shape, a sensor platform 7 supporting an odor sensor S, and a circuit 8 for the odor sensor S provided on a top portion of the sensor platform 7.

The sensor platform 7 is formed of a Teflon (registered trademark) or some other material to which it is difficult for odors to adhere, and is provided with a receptacle support hole 9 on a bottom surface, with the odor sensor S being provided in the middle of an inner bottom portion 10 of the receptacle support hole 9 so that a detector portion S' of the odor sensor S protrudes into the receptacle support hole 9.

A sample receptacle 11 is formed of Teflon registered trademark or some other material the same as the sensor platform 7 and to which it is difficult for odors to adhere and is formed from a main receptacle unit 12 which is cylindrical in shape with the bottom end closed, and a top plate 13 that can close the open portion of the main receptacle unit 12. The top plate 13 can be engaged and detached with the main receptacle unit 12 by a screw 14. The central portion of the top plate 13 is provided with a small opening 15 that is large enough for the detector portion S' of the odor sensor S engaging in the receptacle support hole 9 to be inserted. A sample 23 to be measured is housed in the main receptacle unit 12.

In the outer periphery of the main receptacle unit 12 is formed a thread 17 that engages with a thread 16 on the external housing 6 so that this engagement tightly supports an upper portion of the sample receptacle 11 to the inner surface of the receptacle support hole 9. In addition, in the inner bottom portion 10 of the receptacle support hole 9 are formed air exhaust holes 18, 18 in order to exhaust the air when the sample receptacle 11 is engaged. Moreover, instead of the thread 16 and the thread 17, the support means for the sample receptacle 11 can use a friction engagement using O-rings or the like, or some other suitable means.

Figure 3:
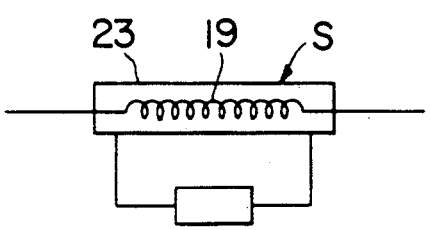
FIG. 3 is a view indicating the configuration of the odor sensor shown in FIG. 1.

As shown in FIGS. 1 and 3, the odor sensor S has sensors SX and SY of a type known in the art, and that have resistance heating units 19 covered by a metallic oxide 23 that has tin dioxide ($SnO_2$) as the main component as shown in FIG. 3.

Figure 4:
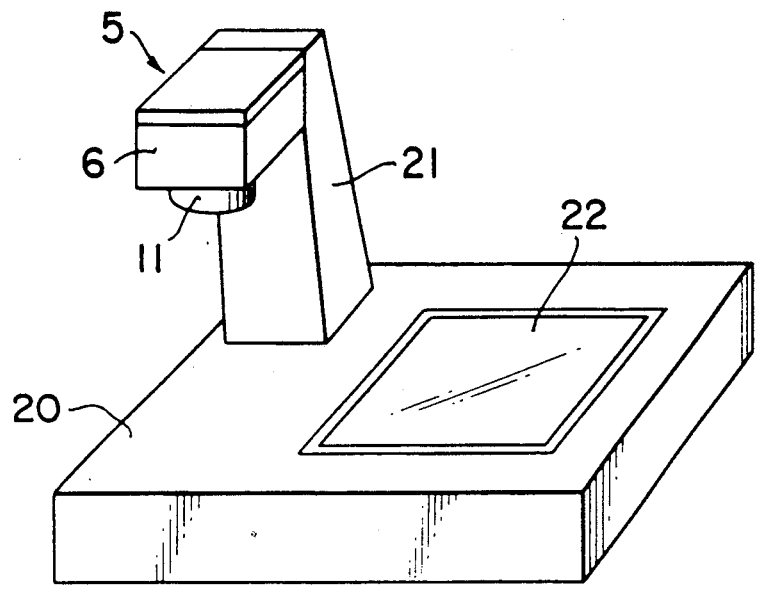
FIG. 4 is a perspective view indicating a specific embodiment of a volatile component detector apparatus according to the present invention.
Figure 12:
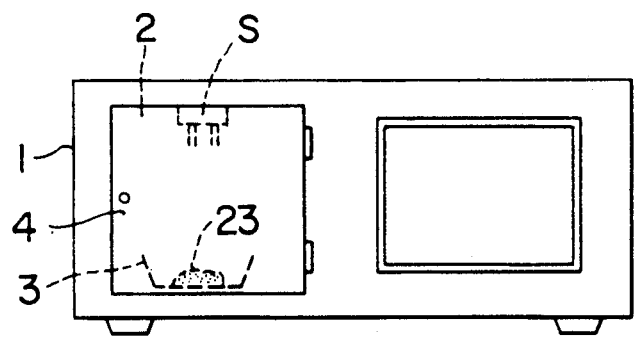
FIG. 12 is a frontal elevational view of a conventional detector apparatus.

FIG. 4 indicates an example of a specific configuration of a detector apparatus using the present invention. A support column 21 stands on one side of a base 20 and has the external housing 6 of the detector unit 5 fixed to an upper portion so that the sample receptacle 11 can be attached to and removed from the lower side. The other half of the base 20 is provided with an X-Y recorder 22 for the odor sensor S and which can be used stably on a tabletop or the like.

The following is a description of the operation of the embodiment described above.

When measurement is performed, the top plate 13 of the sample receptacle 11 is removed and an appropriate amount of the sample 23 to be measured is placed inside the main receptacle unit 12, the top plate 13 is closed and immediately after, the main receptacle unit 12 is screwed into the receptacle support hole 9 from the underside of the external housing 6 of the detector unit 5. So that as shown in FIG. 1, the detector portion S' of the odor sensor S is inserted to inside the small opening 15 of the top plate 13 and so that the upper surface of the top plate 13 of the sample receptacle 11 is supported in close contact with the lower surface of the inner bottom portion 10 of the receptacle support hole 9. By this, the volatile components dispersed from the sample 23 to be measured and inside the main receptacle unit 12 are brought into contact with the detector portion S' of the odor sensor S when they rise upwards inside the sample receptacle 11, and the output from the odor sensor S is then measured.

When the measurement has been completed, the sample receptacle 11 is removed, the top plate 13 is removed and the sample 23 that was measured is discarded. The sample receptacle 11 is cleaned with a neutral cleaning agent and dried for about five minutes to completely deodorize it. In addition, while the measurement is being performed, the side of the detector unit 5 has practically all of its inner surface covered by the outer surface of the sample receptacle 11 and so there is no adhering of odor while the measurement is being performed. It is only necessary to deodorize in the vicinity of the odor sensor S and the following measurement can be proceeded with after only a short time.

Figure 5:
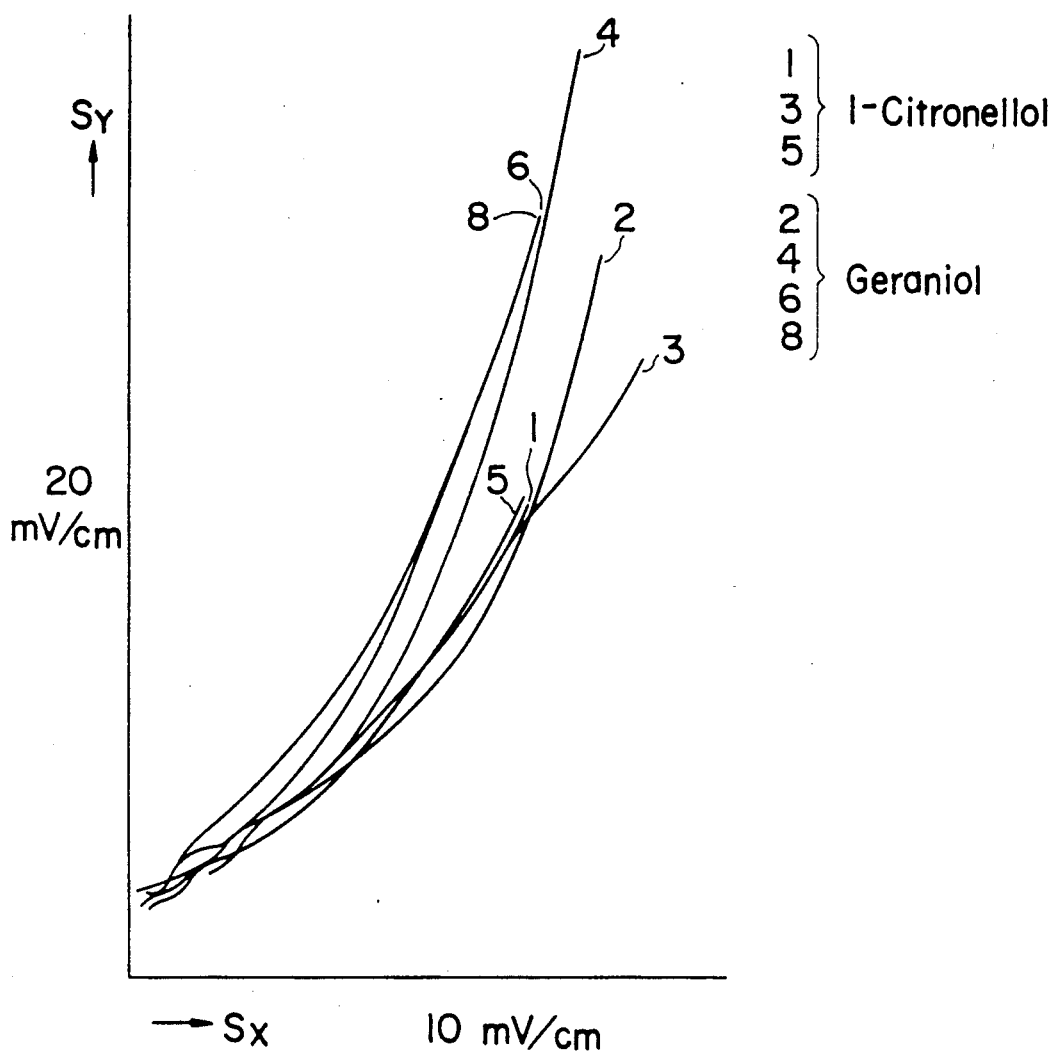
FIG. 5 through FIG. 7 are graphs indicating results of measurement, with FIG. 5 and FIG. 6 indicating the results for the case of a conventional detector apparatus, and FIG. 7 indicating the results for the case of the detector apparatus according to the present invention.
Figure 6:
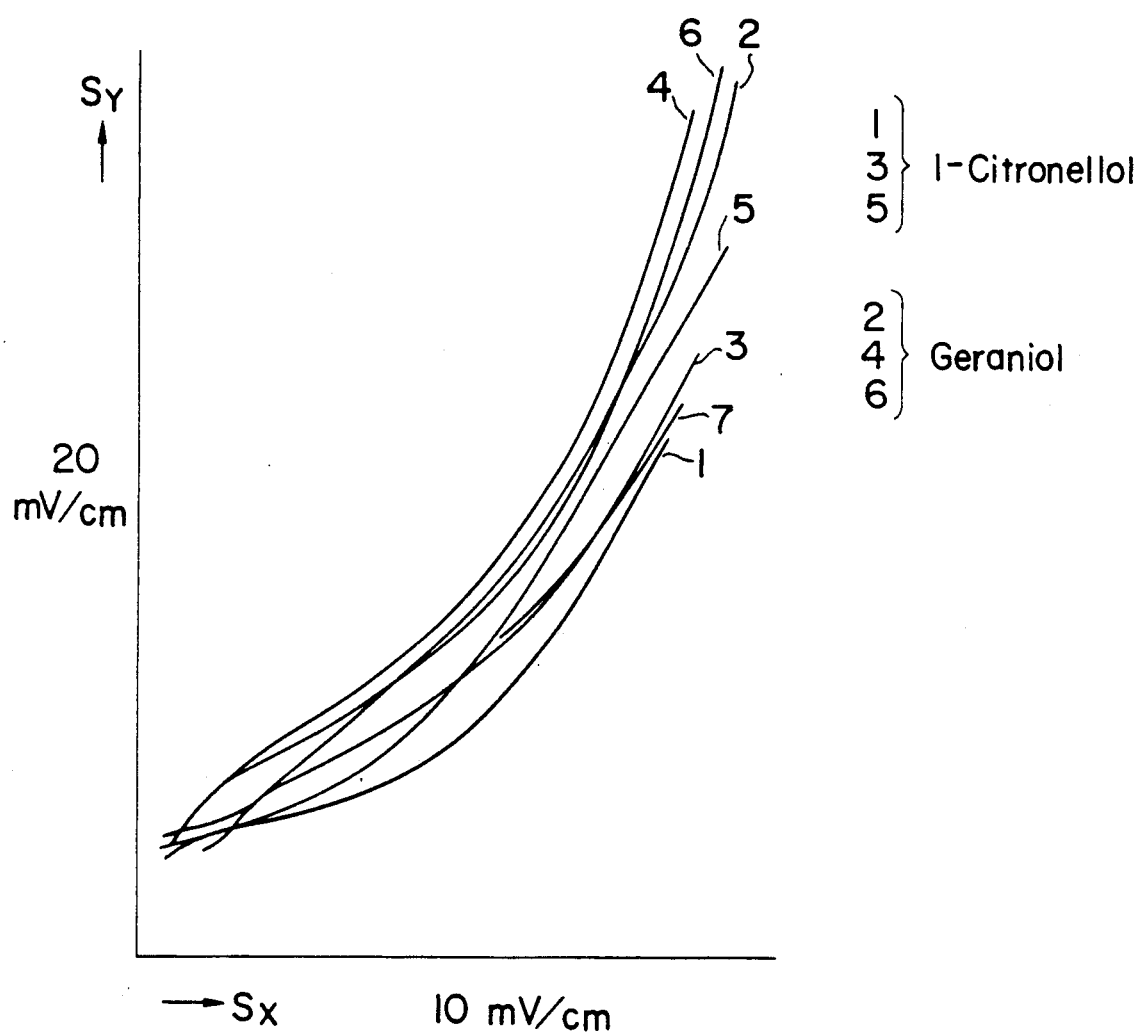
Figure 7:
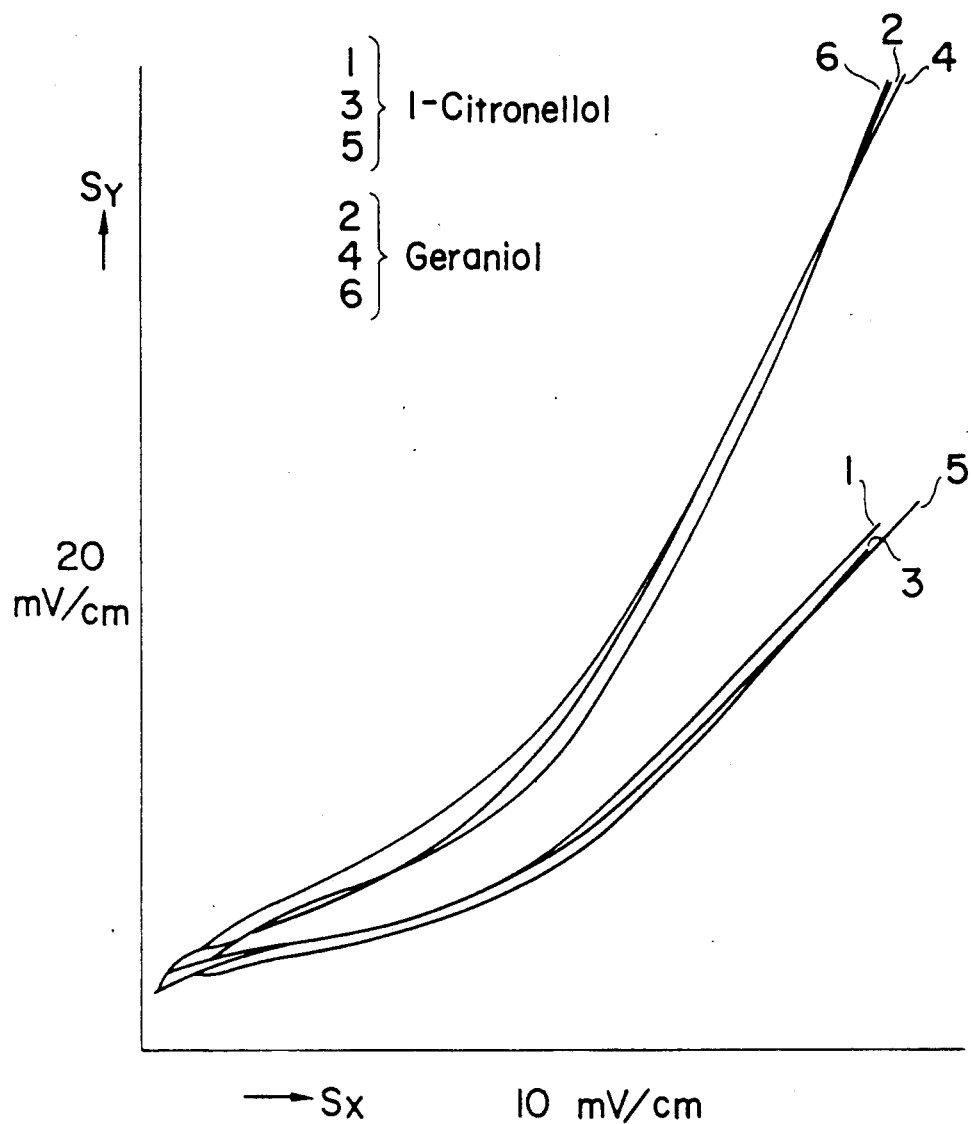

FIG. 5 and FIG. 6 are graphs of the results from an X-Y recorder for alternate measurements of two types of food aromatics (Geraniol and 1-Citronellol), using a conventional detection apparatus, while FIG. 7 is a graph of the same obtained using the present invention. As can be seen from the graphs indicated in FIG. 5 and FIG. 6, with the conventional detection apparatus, the measurements for the aromatic (1-Citronellol) measured 1st, 3rd and 5th, and the aromatic (Geraniol) measured 2nd, 4th and 6th both show large errors due to the influence of alternate residual odors, and this is to the extent that it is practically impossible to distinguish between the two. However, as can be seen in FIG. 7, the measurements according to the present invention enable the clear identification every time of the two aromatics with there being little interference and practically no measurement error.

Moreover, Geraniol ($C_{10}H_{18}O$) is an alcohol relating to the non-cyclic monoterpenes and is used as an aromatic for rose fragrance, while Citronellol ($C_{10}H_{20}O$) is an alcohol relating to the non-cyclic monoterpenes and is also used as an aromatic for rose fragrance.

Figure 8:
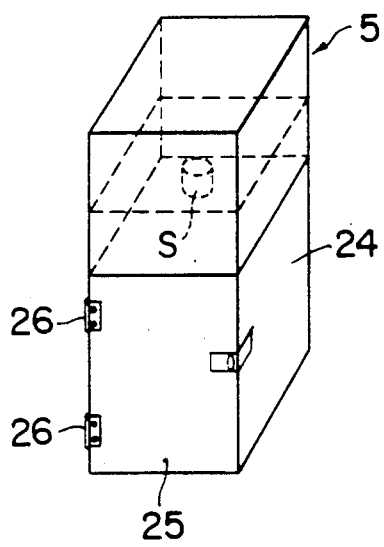
FIG. 8 is a perspective view of a variation of the detector apparatus according to the present invention.
Figure 9:
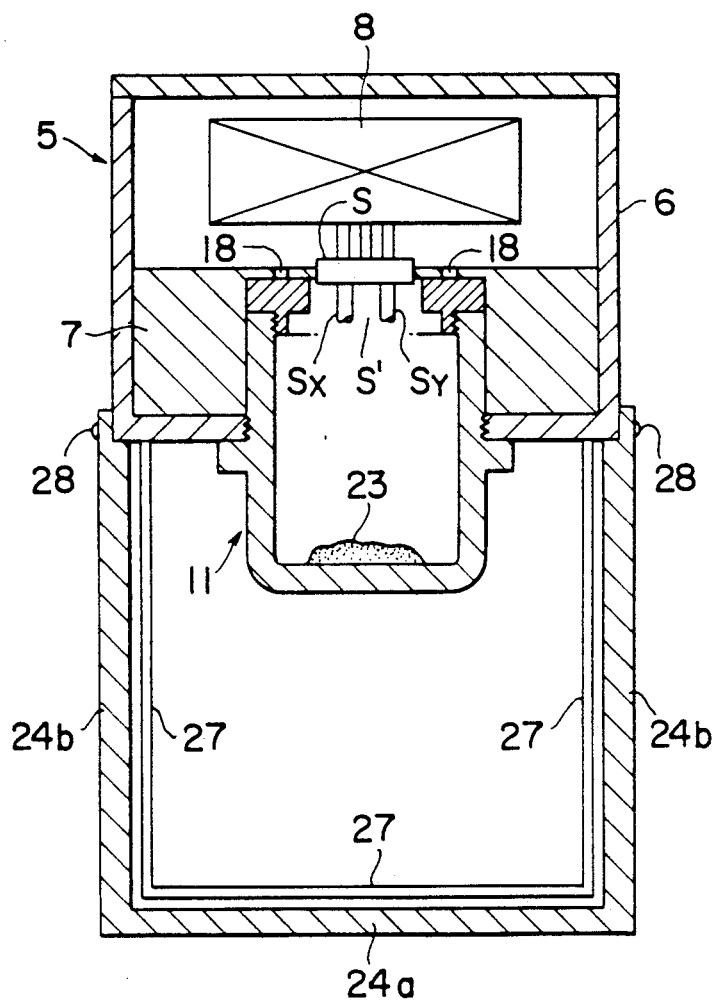
FIG. 9 is a longitudinal sectional view of the detector apparatus shown in FIG. 8.

FIG. 8 and FIG. 9 indicate variations of the configuration where a covering box 24 covers a lower portion of the detector unit 5 in order to heighten the reproducibility of odor detection, without there being any influence of odors in the atmosphere around the odor sensor S when the sample is exchanged.

This is to say that the as indicated by the external view in FIG. 8 and the cross section in FIG. 9, the covering box 24 is mounted in an airtight manner to the bottom portion of the detector unit 5. This covering box 24 has a door 25 on one side and this door 25 can open and close around a hinge 26 so that opening this door 25 enables the sample receptacle 11 to be placed in and taken out of the sample receptacle 11 inside the covering box 24.

The inner surfaces of the bottom portion 24a and the side wall portion 24b and including the inner surface of the door 25 (and desirably including the bottom surface of the top portion) have affixed to them a sheet-type of absorption material 27 such as activated charcoal fiber for example, so that odors inside the covering box 24 are absorbed and the inside of the covering box 24 is deodorized. The mounting of this covering box 24 to the detector unit 5 is performed by engaging the upper periphery with the lower portion of the detector unit 5 in an airtight manner and as indicated in FIG. 9, and by tightening the thread 28 from the outside. However, some other means of mounting can be used instead.

According to this embodiment, nnlx the air inside the covering box 24 need be cleaned and since a static status is maintained, there is no influence to the surface temperature of the odor sensor S and so the zero point can be held.

Figure 10:
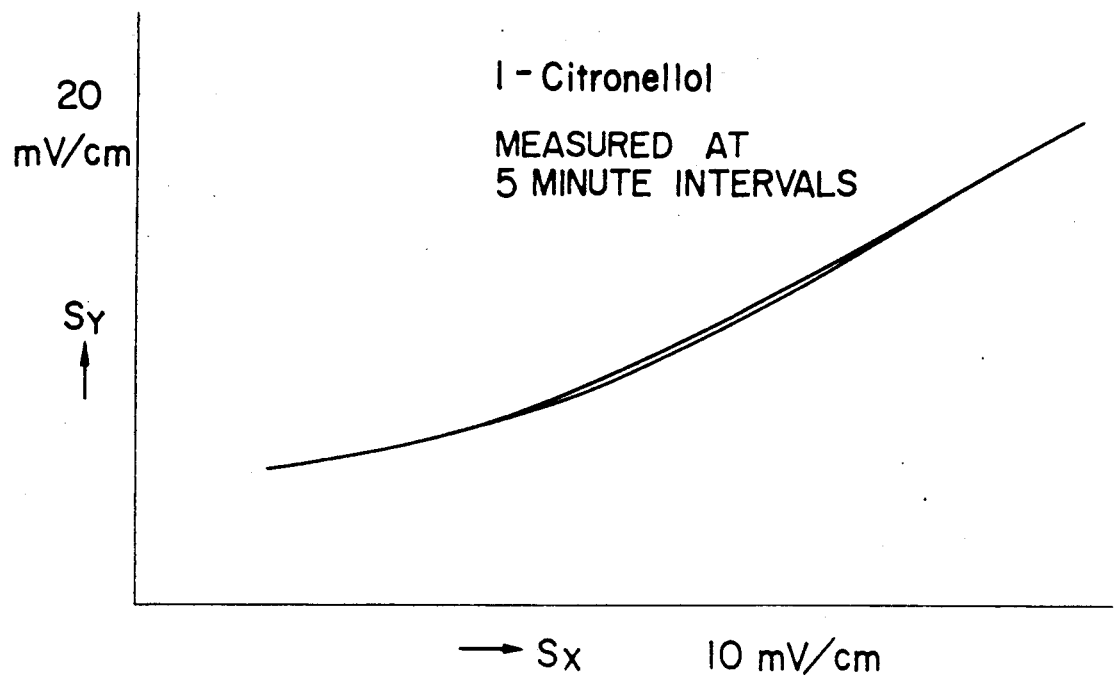
FIG. 10 and FIG. 11 are graphs indicating the results of measurement according to the detector apparatus indicated in FIG. 8.

FIG. 10 indicates the results of measurements performed when the zero point of the sensors SX and SY have been made to coincide when for consecutive measurements made for 1-Citronellol at five minute intervals. If the zero point is made to coincide in this manner, then the measurement results (output) are in good agreement, there is excellent reproducibility, and other factors such as residual odor, the influence of temperature do not influence the accuracy of measurement.

Figure 11:
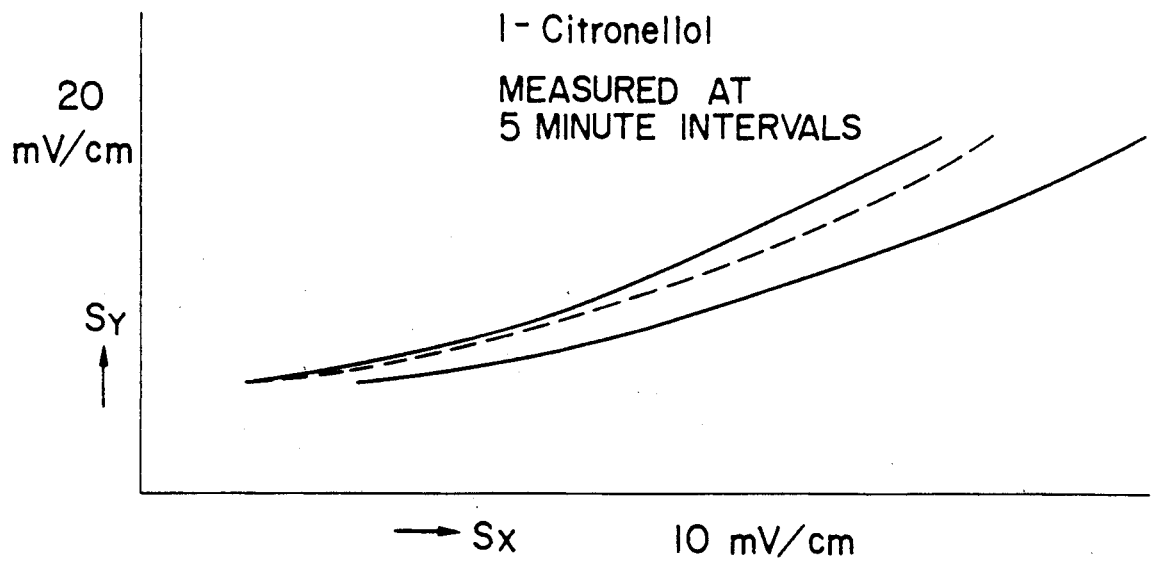

FIG. 11 indicates the measurement results for the case where repeated measurement is performed without the covering box 24 and without making the zero point coincide. Here, there is a discrepancy in the output line graph and there is still a discrepancy in the output even if the recorder position is used to displace the results as indicated by the dotted line to make the zero point coincide.

According to the present invention as has been described above, the sample receptacle into which the sample to be measured has been inserted, is engaged with and supported by the detector apparatus so that the detector portion of the odor sensor enters the sample receptacle through the opening in the sample receptacle. Therefore, the volatile components dispersed from the sample to be measured and contained inside the sample receptacle promptly reach the odor sensor so that the measurement can commence almost at the same time as the sample receptacle is mounted, thereby reducing the time required for measurement and increasing the work efficiency. In addition, having the sample receptacle engaged with and supported while the measurement is being performed, and covering the inside surface of the receptacle support hole on the side of the detector apparatus by the outer surface of the sample receptacle eliminates the adhering of the odor of the sample to the inner surface of the receptacle holder when the measurement is being performed. Because of this, it is possible to return the detection apparatus to a deodorized state soon after the measurement has been completed and the sample receptacle removed. This enables the following measurement to be performed soon after and serves to further increase the work efficiency while at the same time practically eliminating the influence that residual odor has on the following measurement to consequently and greatly improve the accuracy of measurement.

If a covering box covers the sample receptacle at the lower portion of the detector apparatus and the inner surface of this covering box is coated with a deodorizing material, then it is possible to practically eliminate the influence of odors in air that enters while the sample is being exchanged, therefore enabling the odor sensor to be zeroed and improving the reproducibility of measurement and thus improving the accuracy of measurement.

While the presently preferred embodiments of the present invention have been shown and described, it is to be understood that these disclosures are for the purpose of illustration and that various changes and modifications may be made without departing from the scope of the invention as set forth in the appended claims.

What is claimed is:

1. A volatile component detector having a sensor platform fixed inside a main body of a volatile component detector comprising:

a sample receptacle which is removably securable to a bottom surface of a sensor platform, said sensor platform having a receptacle support hole for receipt of said sample receptacle when said receptacle is secured to said bottom surface, an odor sensor mounted on an inner bottom of the receptacle receiving hole and having its detector portion protruding into said hole, said sample receptacle having a top plate having an opening therethrough which enables the insertion of said protruding detector portion into said sample receptacle through said opening when the sample receptacle is disposed within said receptacle receiving hole, and a covering box mounted at a lower portion of the sensor platform in an airtight manner so as to enclose said sample receptacle and having an absorption material of activated charcoal fiber on an inner surface thereof.

2. The volatile component detector of claim 1, wherein said inner bottom of said receptacle receiving hole includes an air exhaust hole allowing exhausting of the air from said receptacle receiving hole when said sample receptacle is received therein.

* * * * *